(12) United States Patent
Terinek et al.

(10) Patent No.: US 8,895,757 B2
(45) Date of Patent: Nov. 25, 2014

(54) PROCESS FOR THE PREPARATION OF PYRAZOLE CARBOXYLIC ACID AMIDES

(75) Inventors: Miroslav Terinek, Muenchwilen (CH); Dominik Faber, Muenchwilen (CH); Stefan Koenig, Muenchwilen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/981,913

(22) PCT Filed: Jan. 25, 2012

(86) PCT No.: PCT/EP2012/051075
§ 371 (c)(1),
(2), (4) Date: Jul. 25, 2013

(87) PCT Pub. No.: WO2012/101139
PCT Pub. Date: Aug. 2, 2012

(65) Prior Publication Data
US 2013/0310592 A1    Nov. 21, 2013

(30) Foreign Application Priority Data

Jan. 25, 2011    (EP) ..................... 11151965

(51) Int. Cl.
*C07D 231/14*    (2006.01)
(Continued)

(52) U.S. Cl.
CPC ............. *C07C 231/14* (2013.01); *C07C 329/04* (2013.01); *C07C 251/56* (2013.01);
(Continued)

(58) Field of Classification Search
CPC ............................ C07D 231/14; C07C 251/56
USPC ....................... 548/374.1; 558/262
See application file for complete search history.

(56) References Cited

FOREIGN PATENT DOCUMENTS

WO    2007/048556    5/2007
(Continued)

OTHER PUBLICATIONS

International Search Report, International Application No. PCT/EP2012/051075, completion date: Mar. 2, 2012.

*Primary Examiner* — Kamal Saeed
(74) *Attorney, Agent, or Firm* — R. Kody Jones

(57) ABSTRACT

The invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide by acylating the oxime oxygen of the compound of formula (VIII), in the presence of a solvent and an acylating agent of formula (XI) $R_1C(X)$—Cl (XI); wherein X is oxygen or sulfur; $R_1$ is chloro if X is oxygen or sulfur; or R1 is $C_1$-$C_6$alkoxy, $CH_3$—$C(=CH_2)$—O—, phenoxy or trichloromethoxy if X is oxygen; and a) if $R_1$ is chloro and the compound of formula (XI) was added to the compound of formula (VIII); reacting the so obtained product of formula (XIIa) wherein X is oxygen or sulfur; with the compound of formula (IX) b) if $R_1$ is chloro and the compound of formula (VIII) was added to the compound of formula (XI); or $R_1$ is $C_1$-$C_6$alkoxy, $CH_3$—$C(=CH_2)$—O—, phenoxy or trichloromethoxy if X is oxygen; reacting the so obtained product of formula (XII) wherein X is oxygen or sulfur; $R_1$ is chloro if X is oxygen or sulfur; or $R_1$ is $C_1$-$C_6$alkoxy, $CH_3$—$C(=CH_2)$—O—, phenoxy or trichloromethoxy if X is oxygen; with the compound of formula (IX).

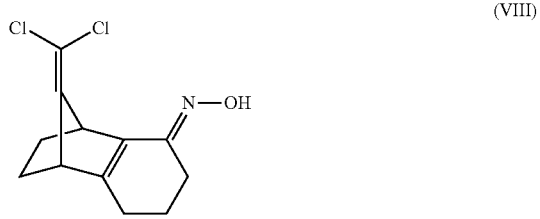

(VIII)

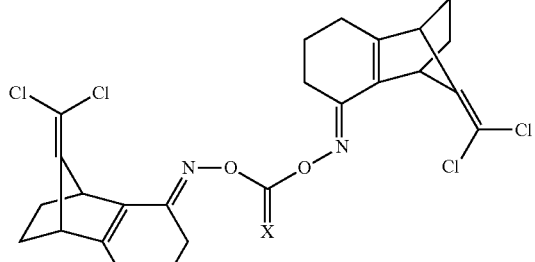

(XIIa)

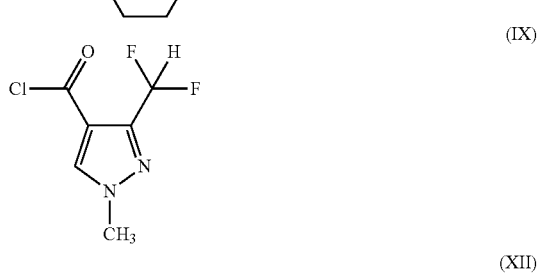

(IX)

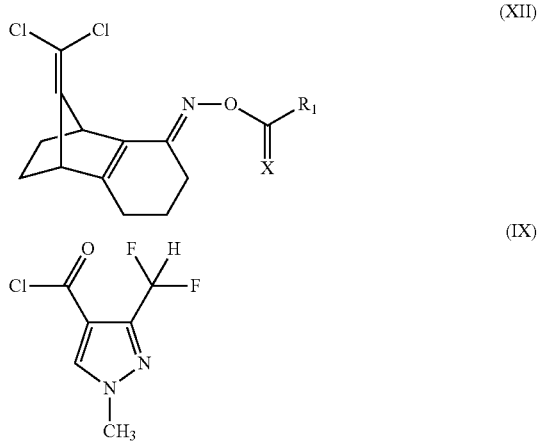

(XII)

(IX)

8 Claims, No Drawings

(51) Int. Cl.
*C07C 251/56* (2006.01)
*C07C 329/04* (2006.01)
*C07C 231/14* (2006.01)
*C07C 329/02* (2006.01)
*C07C 251/64* (2006.01)

(52) U.S. Cl.
CPC ............. *C07C 329/02* (2013.01); *C07C 251/64* (2013.01); *C07C 2103/66* (2013.01)
USPC ........................................ 548/374.1; 558/262

(56) References Cited

FOREIGN PATENT DOCUMENTS

| | | |
|---|---|---|
| WO | 2009/138375 | 11/2009 |
| WO | 2010/072631 | 7/2010 |
| WO | 2011/015416 | 2/2011 |
| WO | 2011/131544 | 10/2011 |
| WO | 2011/131545 | 10/2011 |
| WO | 2011/131546 | 10/2011 |

PROCESS FOR THE PREPARATION OF PYRAZOLE CARBOXYLIC ACID AMIDES

This application is a 371 of International Application No. PCT/EP2012/051075 filed Jan. 25, 2012, which claims priority to EP 11151965.8 filed Jan. 25, 2011, the contents of which are incorporated herein by reference.

PROCESS FOR THE PREPARATION OF PYRAZOLE CARBOXYLIC ACID AMIDE

The present invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide.

The compound 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties is described, for example, in WO 2007/048556.

According to WO 2011/015416, 3-difluoromethyl-1-methyl-1H-pyrazole-4-carboxylic acid (9-dichloromethylene-1,2,3,4-tetrahydro-1,4-methano-naphthalen-5-yl)-amide can be prepared by a) reacting the compound of formula II

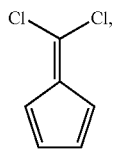

(II)

in the presence of a catalyst in a suitable organic solvent with the compound of formula III

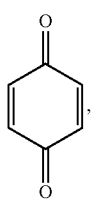

(III)

to the compound of formula IV

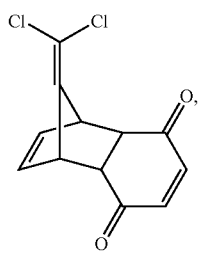

(IV)

b) hydrogenating the compound of formula IV in the presence of a metal catalyst to the compound of formula V

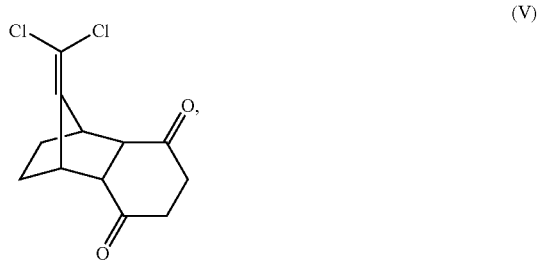 [SMILES: O=C1CCC(=O)C2C3CCC(C3=C(Cl)Cl)C12]

(V)

c) reducing the compound of formula V in the presence of a reducing agent to the compound of formula VI

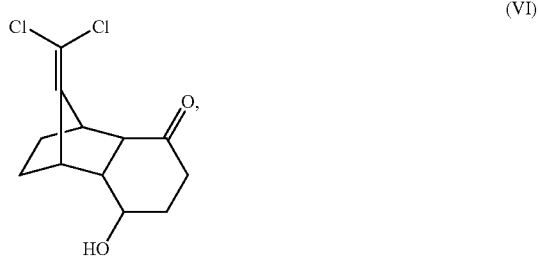 [SMILES: O=C1CCC(O)C2C3CCC(C3=C(Cl)Cl)C12]

(VI)

d) dehydrating the compound of formula VI in the presence of an acid to the compound of formula VII

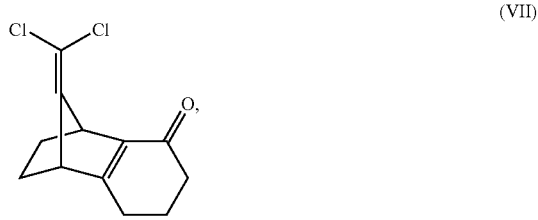 [SMILES: O=C1CCCC2=C1C1CCC2C1=C(Cl)Cl]

(VII)

e) reacting the compound of formula VII with hydroxylamine to the compound of formula VIII

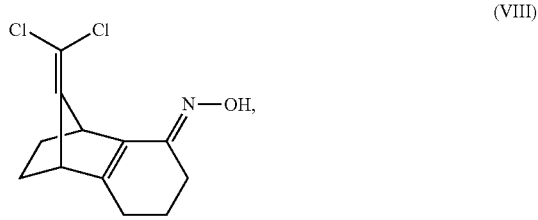 [SMILES: O/N=C1\CCCC2=C1C1CCC2C1=C(Cl)Cl]

(VIII)

and f) acylating the oxime oxygen of the compound of formula VIII in the presence of a solvent and an acid chloride (for example acetyl chloride, pivaloyl chloride, benzoyl chloride or chloroacetyl chloride) or acyl anhydride like acetic anhydride or pivaloyl anhydride and finally reacting the so obtained product with the compound of formula IX

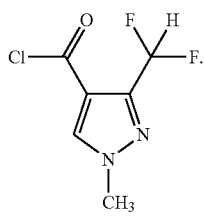
(IX)

Surprisingly, it has now been found that the yield of the acylation reaction (step f) can be significantly improved by the selection of a specific acylation reagent.

Thus, according to the present invention, there is provided a process for the preparation of the compound of formula I

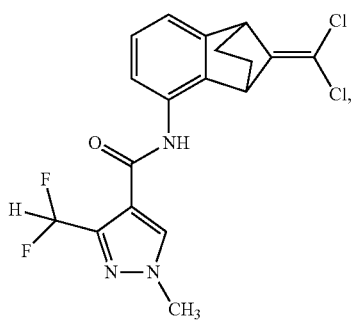
(I)

which process comprises acylating the oxime oxygen of the compound of formula VIII

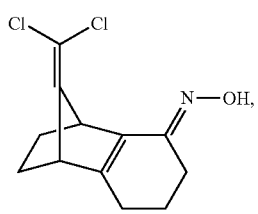
(VIII)

in the presence of a solvent and an acylating agent of formula XI

R$_1$—C(X)—Cl    (XI), wherein X is oxygen or sulfur;

R$_1$ is chloro if X is oxygen or sulfur; or

R$_1$ is C$_1$-C$_6$alkoxy, CH$_3$—C(=CH$_2$)—O—, phenoxy or trichloromethoxy if X is oxygen;

and a) if R$_1$ is chloro and the compound of formula XI was added to the compound of formula VIII; reacting the so obtained product of formula XIIa

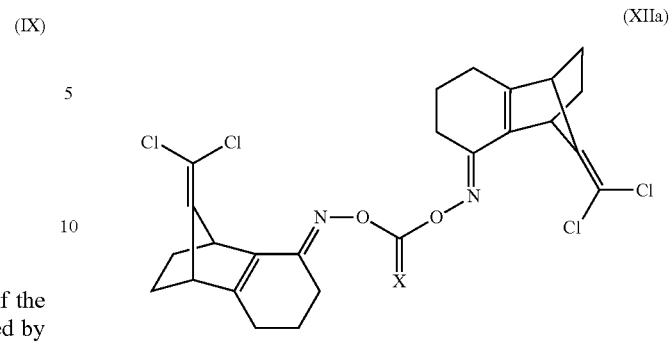
(XIIa)

wherein X is oxygen or sulfur; with the compound of formula IX

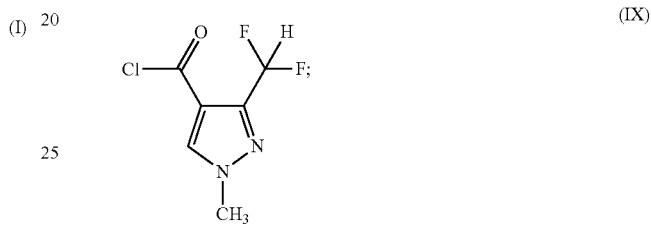
(IX)

or b) if R$_1$ is chloro and the compound of formula VIII was added to the compound of formula XI; or R$_1$ is C$_1$-C$_6$alkoxy, CH$_3$—C(=CH$_2$)—O—, phenoxy or trichloromethoxy if X is oxygen; reacting the so obtained product of formula XII

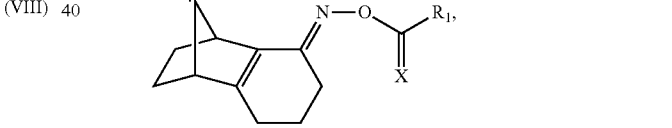
(XII)

wherein X is oxygen or sulfur;

R$_1$ is chloro if X is oxygen or sulfur; or

R$_1$ is C$_1$-C$_6$alkoxy, CH$_3$—C(=CH$_2$)—O—, phenoxy or trichloromethoxy if X is oxygen; with the compound of formula IX

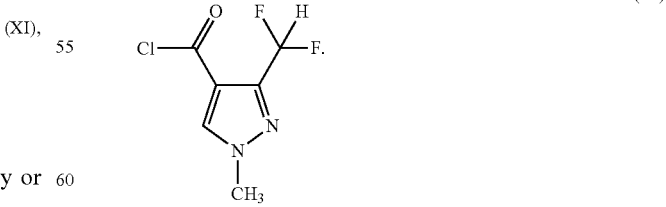
(IX)

The alkoxy groups occurring in the definitions of the substituents can be straight-chain or branched and are, for example, methoxy, ethoxy, n-propoxy, n-butoxy, n-pentoxy, n-hexyloxy, iso-propoxy, n-butoxy, sec-butoxy, iso-butoxy or tert-butoxy.

A preferred embodiment of the process according to the invention comprises acylating the oxime oxygen of the compound of formula VIII

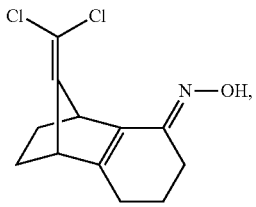

in the presence of a solvent and an acylating agent of formula XI $R_1$—C(X)—Cl  (XI), wherein X is oxygen; $R_1$ is $C_1$-$C_6$alkoxy, $CH_3$—C(=$CH_2$)—O—, phenoxy or trichloromethoxy; preferably $C_1$-$C_6$alkoxy, phenoxy or trichloromethoxy; and reacting the so obtained product of formula XII

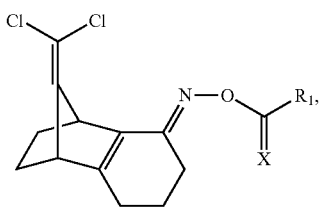

wherein X is oxygen; $R_1$ is $C_1$-$C_6$alkoxy, $CH_3$—C(=$CH_2$)—O—, phenoxy or trichloromethoxy;
with the compound of formula IX

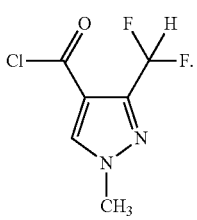

Preferred acylating agents of formula XI are those, wherein $R_1$ is methoxy, ethoxy, isopropoxy, phenoxy or isopropenyloxy and X is oxygen, more preferably $R_1$ is methoxy, ethoxy, isopropoxy or phenoxy and X is oxygen, in particular $R_1$ is ethoxy.

The compounds of formula XII are novel, were especially developed for the process according to the invention and therefore constitute a further object of the invention. Preferred compounds formula XII are those, wherein $R_1$ is methoxy, ethoxy, isopropoxy, phenoxy or isopropenyloxy and X is oxygen, more preferably $R_1$ is methoxy, ethoxy, isopropoxy or phenoxy and X is oxygen, in particular $R_1$ is ethoxy.

The process according to the invention consists of two chemical transformations: reaction of the oxime oxygen with the acylating agent followed by in situ transformation of the acylated derivative to the compound of formula I by reaction with 1.0 to 1.3 equivalents preferably 1.05 equivalents of the compound of formula IX advantageously in the presence of an acid (preferably HCl, $H_2SO_4$ or $CH_3SO_3H$, most preferred $CH_3SO_3H$). The addition of the acid accelerates the formation of the compound of formula I and therefore significantly reduces the reaction time.

The acylation is advantageously performed in the presence of a base. The base is used in an amount of 1 to 1.5 equivalents with respect to the compound of formula VIII, in particular in an amount of 1.2 equivalents. Suitable bases for the acylation are pyridine or tertiary amines like triethylamine. Triethylamine is especially preferred as a base. Preferred reaction temperatures for the process are from 60 to 150° C., in particular 85-125° C., most preferably 95 to 115° C. In another preferred embodiment of the present invention the reaction is performed at a temperature from 130 to 135° C. with an acylation agent of the formula XI wherein $R_1$ is ethoxy and X is oxygen.

Suitable solvents are toluene, dioxane, tetrahydrofurane, xylene, chlorobenzene or acetonitrile. Most preferred solvent is xylene.

If the acylation agent is phosgen or thiophosgen, the structure of the compound obtained from the reaction of the oxime of formula VIII with phosgen or thiophosgen depends on the order of addition of the reactants.

If the compound of formula XI, wherein $R_1$ is chloro and X is oxygen or sulfur is added to the compound of formula VIII; the compound of formula XIIa

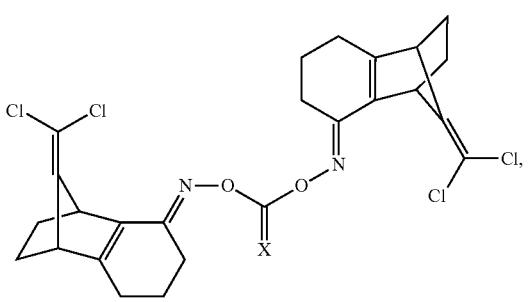

wherein X is oxygen or sulfur; is obtained.

If the compound of formula VIII is added to the compound of formula XI wherein $R_1$ is chloro and X is oxygen or sulfur; the compound of formula XII

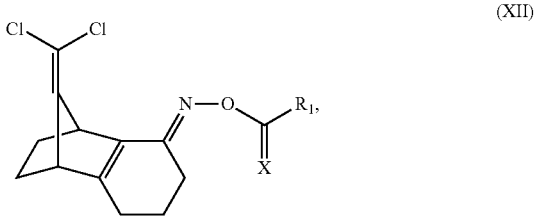

wherein X is oxygen or sulfur and $R_1$ is chloro; is obtained.

For compounds of formula XI, wherein $R_1$ is $C_1$-$C_6$alkoxy, $CH_3$—C(=$CH_2$)—O—, phenoxy or trichloromethoxy if X is oxygen; the compound of formula XII was obtained independently from the order of addition of the reactants.

The compounds of formula XIIa are novel, were especially developed for the process according to the invention and therefore constitute a further object of the invention. In a preferred compound of formula XII, X is oxygen.

It was also found that the addition of CH₃SO₃H accelerates the formation of the compound of formula I and therefore significantly reduces the reaction time.

The compound of formula IX is known and commercially available. The compound is disclosed, for example, in U.S. Pat. No. 5,093,347.

PREPARATORY EXAMPLES

The compound of formula VIII can be prepared according to WO 2011/015416 as follows:

Example P1

Preparation of the Compound of Formula IV

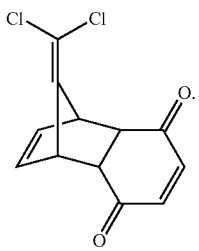

(IV)

Catalyst Solution:

To a stirred suspension of AlI₃ (60.0 g, 0.45 mol) in toluene (200 g) was added tetrahydrofurane (46.0 g, 0.64 mol) dropwise at 20-25° C. under inert atmosphere (nitrogen). The clear solution of catalyst was stored at ambient temperature.

Diels-Alder Cycloaddition:

A glass reactor was loaded with a cold solution of 6,6-dichlorofulvene in toluene (858 g, 0.479 mol, 8.2%) and 1,4-benzoquinone (56.9 g, 0.526 mol). The reactor content was cooled to −9° C. while being stirred under inert atmosphere (nitrogen). Catalyst solution (40 g, contains 7.8 g AlI₃) was added into the reactor withing 30 min at −9° C., then an additional amount of catalyst solution (10 g, contains 2.0 g AlI₃) was added withing 60 min. After stirring for 3.5 hours at −9° C., the reaction mixture was quenched by dropwise addition of ethanol (70 ml) at −9° C. The reaction mass was stirred at −9° C. for 30 min and filtered. The product was washed with cold ethano/toluene mixture (2:1, 360 ml) and dried in vacuum.

Yield 102 g (83%).

¹H NMR (CDCl₃, 400 MHz) δ 3.40 (m, 2H), 4.09 (m, 2H), 6.21 (t, J=2.0 Hz, 2H), 6.66 (s, 2H). ¹³C NMR (CDCl₃, 75 MHz) δ47.5, 49.6, 103.4, 134.8, 142.6, 147.6, 196.6.

6,6-dichlorofulvene of formula II is known and disclosed e.g. in Chemical Communications, 20, 1293 (1971). 6,6-dichlorofulvene of formula II can be, for example, prepared by reacting cyclopentadiene with CCl₄ in the presence of a metal catalyst selected from ruthenium, copper, iron, palladium and rhodium complexes to the compound of formula X

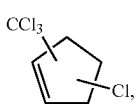

(X)

and reacting the compound of formula X with a base in an appropriate solvent to 6,6-dichlorofulvene.

1,4-benzoquinone is known and commercially available.

Example P2

Preparation of the Compound of Formula V

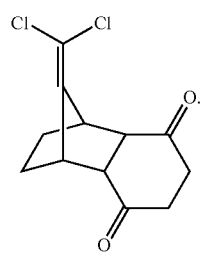

(V)

1 l two-neck flask was charged with compound of formula IV (36.6 g, 0.143 mol) and 5%-Rh/C (3.0 g, 0.42 mol % Rh, water content 58.0%). The flask was evacuated and refilled with nitrogen two times followed by addition of tetrahydrofurane (600 ml). Then the reaction mixture was evacuated until tetrahydrofurane boils and refilled with hydrogen from a balloon two times. Consumption of hydrogen was monitored using a bubble counter. Intensive stirring of the reaction mixture is essential for fast hydrogenation. The conversion was monitored by ¹H NMR and was complete after 7 hours. At this time consumption of hydrogen became very slow. The reaction mixture was filtered through a glass frit filter. The filter cake, which contained undissolved product, was washed with tetrahydrofurane few times to dissolve it. The combined filtrate was evaporated and the remaining crystalline residue was stirred with methanol (150 ml) for about 15 min at ambient temperature, then cooled in an ice bath, stirred for additional 15 min, filtered, washed with methanol and dried in air. Yield 32.7 g (88%).

¹H NMR (CDCl₃, 400 MHz) δ 1.47-1.53 (m, 2H), 1.72-1.79 (m, 2H), 2.51-2.60 (m, 2H), 2.82-2.92 (m, 2H), 3.20 (m, 2H), 3.37 (m, 2H). ¹³C NMR (CDCl₃, 100 MHz) δ 23.7, 38.8, 43.9, 50.5, 106.9, 144.0, 207.8.

Example P3

Preparation of the Compound of Formula VI

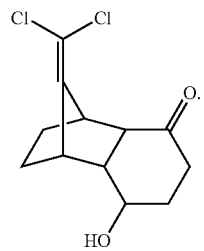

(VI)

A mixture of the compound of formula V (47.3 g, 0.183 mol), methanol (300 ml) and tetrahydrofurane (300 ml) was cooled to 0-5° C. in an ice bath. Sodium borohydride (2.17 g, 0.0573 mol) was added in portions during 1.5 hours. The reaction mixture was allowed to warm to ambient temperature and the solvent was removed by rotary evaporation. The residue was partitioned between methyl-tert-butylether (1000 ml) and 0.5N HCl (300 ml). The organic phase was separated, filtered and evaporated. The residue was dried in vacuum.

Yield 46.9 g (98%, 9:1 mixture of isomers at the hydroxyl).

$^1$H NMR (CDCl$_3$, 400 MHz) δ (major isomer) 1.58-1.72 (m, 3H), 1.84 (bs, 1H), 2.04 (m, 2H), 2.20-2.35 (m, 2H), 2.48-2.55 (m, 1H), 2.74 (m, 2H), 3.12 (m, 1H), 3.28 (m, 1H), 4.41 (m, 1H).

Example P4

Preparation of the Compound of Formula VII

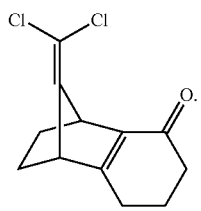

(VII)

Finely powdered compound of formula VI (26.25 g, 0.1005 mol) was added within 10 min to an intensively stirred 96% sulphuric acid (80 ml) at ambient temperature (cooling with a water bath). The reaction mixture was stirred at the same temperature for 30 min and then poured slowly into a mixture of ice (200 g), ice-cold water (200 ml) and methyl-tert-butylether (250 ml) under vigorous stirring. The organic phase was separated and the water phase was extracted with methyl-tert-butylether (70 ml). The combined extract was washed with 3% solution of sodium bicarbonate (150 ml) and then with brine (100 ml). The organic phase was separated and the solvent was removed by rotary evaporation. The residue was extracted into boiling hexane (100+10+10 ml). The hot solution was filtered through a glass frit filter (slight evacuation) and left for crystallization at ambient temperature. After 1 hour the crystallization mixture was further cooled to 0° C. (ice bath) and kept at this temperature for 30 min. The large crystals formed were filtered, washed with hexane (30 ml) and dried in air.

The mother liquor was concentrated to 15 ml volume and additional crop was collected. Yield 20.7 g (85%).

$^1$H NMR (CDCl$_3$, 400 MHz) δ (major isomer) 1.23-1.32 (m, 2H), 1.88-2.14 (m, 4H), 2.23-2.30 (m, 1H), 2.35-2.57 (m, 3H), 3.49 (m, 1H), 3.87 (m, 1H). $^{13}$C NMR (CDCl$_3$, 100 MHz) δ 23.3, 24.2, 25.0, 25.7, 37.4, 42.2, 49.6, 102.3, 140.7, 149.2, 167.1, 193.7.

Example P5

Preparation of the Compound of Formula VIII

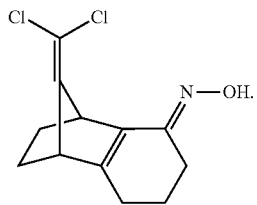

(VIII)

A mixture of compound of formula VII (24.6 g, 0.101 mol), hydroxylamine hydrochloride (8.43 g, 0.121 mol), pyridine (12.0 g, 0.152 mol) and absolute ethanol was stirred at ambient temperature for 4 hours. The reaction mixture was partitioned between ethyl acetate (500 ml) and water (500 ml). The organic phase was separated, washed two times with water (500 ml) and evaporated. The remaining crystalline residue was dried in vacuum. Yield 25.6 g (99%).

$^1$H NMR (DMSO-d6, 400 MHz) δ (major isomer) 1.17 (m, 1H), 1.32 (m, 1H), 1.67 (m, 2H), 1.77-1.92 (m, 2H), 2.14-2.31 (m, 3H), 2.50 (m, 1H), 3.36 (d, J=3.4 Hz, 1H), 3.64 (d, J=3.3 Hz, 1H), 10.70 (s, 1H).

Example P6

Preparation of the Compound of Formula XIIb

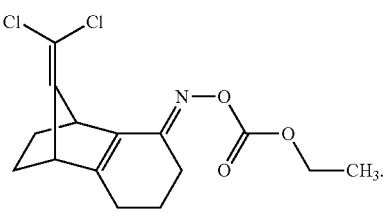

(XIIb)

A mixture of the compound of formula VIII (104.2 g, 0.40 mol) and triethylamine (44.7 g, 0.44 mol) in toluene (400 g) was treated with a solution of ethyl chloroformate (53.2 g, 0.49 mol) in toluene (200 g) at 25° C. within 60 min and stirred at 25° C. for additional 50 min. The reaction mixture was treated with water (150 g). The organic layer was separated, washed with water (50 g) and brine (30 g) and evaporated to dryness. The remaining yellow oil was dissolved in hot ethanol (700 g) and slowly cooled down to 5° C. The resulting precipitate was filtered off, washed with cold ethanol and dried in vacuum. Yield 90.1 g (68%, 99+% purity as determined by quantitative $^1$H NMR and LC analyses).

The mother liquor was evaporated to obtain 43 g of the material which crystallized again from hot ethanol (150 g). The precipitate was filtered off, washed with cold ethanol and dried in vacuum to yield additional 25.7 g (19%, 99+% purity as determined by quantitative $^1$H NMR and LC analyses) of the desired product XIIb.

M. p. 110° C.

$^1$H NMR (CDCl$_3$, 400 MHz) δ (major isomer) 1.24-1.38 (m, 2H), 1.36 (t, J=7.0 Hz, 3H), 1.77-1.85 (m, 2H), 1.87-2.01 (m, 2H), 2.24 (td, J=6.8 and 18.4 Hz, 1H), 2.35-2.51 (m, 2H), 2.75 (td, J=5.8 and 17.2 Hz, 1H), 3.41 (dd, J=0.8 and 3.3 Hz, 1H), 3.98 (d, J=3.0 Hz, 1H), 4.31 (q, J=7.1 Hz, 2H).

$^{13}$C NMR (CDCl$_3$, 100 MHz) δ (major isomer) 14.29, 21.01, 23.46, 23.67, 25.89, 26.08, 43.39, 49.29, 64.52, 101.49, 134.21, 149.42, 153.94, 156.89, 157.45.

Example P7

Preparation of the Compound of Formula XIIc

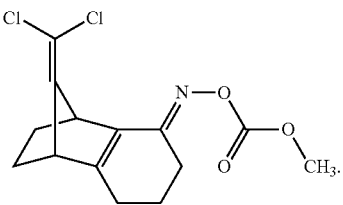

(XIIc)

A mixture of the compound of formula VIII (10.43 g, 0.040 mol) and triethylamine (4.47 g, 0.044 mol) in toluene (50 g) was treated with a solution of methyl chloroformate (4.20 g, 0.044 mol) in toluene (10 g) at 25° C. within 60 min and stirred at 25° C. for additional 90 min. The reaction mixture was treated with water (60 g). The organic layer was separated and the aqueous layer was extracted with toluene (30 g). The combined organic layers were washed with water (50 g) and evaporated. The remaining yellow solid was dried in vacuum. Yield 5.80 g (41%, ca. 90% purity as determined by LC analysis).

The crude material (5.50 g) was recrystallized from hot methanol (90 g) for analytical purposes. The precipitate was filtered off, washed twice with cold methanol and dried in vacuum. Yield 4.70 g (95%, 99+% purity as determined by quantitative $^1$H NMR and LC analyses).

M. p. 159° C.

$^1$H NMR (CDCl$_3$, 400 MHz) δ (major isomer) 1.23-1.37 (m, 2H), 1.77-1.85 (m, 2H), 1.86-2.01 (m, 2H), 2.24 (td, J=6.8 and 18.4 Hz, 1H), 2.37-2.50 (m, 2H), 2.75 (td, J=5.8 and 17.2 Hz, 1H), 3.42 (dd, J=1.3 and 3.3 Hz, 1H), 3.88 (s, 3H), 3.98 (d, J=3.0 Hz, 1H).

$^{13}$C NMR (CDCl$_3$, 100 MHz) δ (major isomer) 21.01, 23.46, 23.64, 25.89, 26.10, 43.39, 49.31, 55.15, 101.56, 134.16, 149.40, 154.54, 157.08, 157.61.

Example P8

Preparation of the Compound of Formula XIId

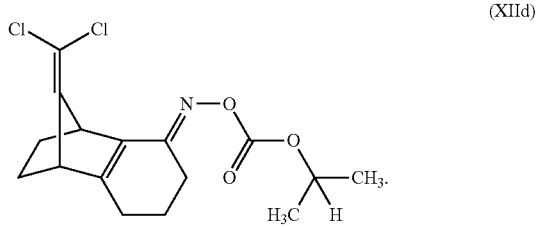 [SMILES: CC(C)OC(=O)O/N=C1\CCCC2=C1C1CCC2C1=C(Cl)Cl]

(XIId)

A mixture of the compound of formula VIII (10.43 g, 0.040 mol) and triethylamine (4.47 g, 0.044 mol) in toluene (50 g) was treated with a 30% (w/w) solution of isopropyl chloroformate in toluene (18.0 g, 0.044 mol) at 25° C. within 60 min and stirred at 25° C. for additional 90 min. The reaction mixture was treated with water (40 g). The organic layer was separated and evaporated to dryness. The remaining yellow solid (13.8 g) was dissolved in hot isopropanol (150 g) and slowly cooled down to 5° C. The resulting precipitate was filtered off, washed with cold isopropanol and dried in vacuum. Yield 11.3 g (82%, 99+% purity as determined by quantitative $^1$H NMR and LC analyses).

M. p. 135° C.

$^1$H NMR (CDCl$_3$, 400 MHz) δ (major isomer) 1.25-1.41 (m, 2H), 1.37 (d, J=7.3 Hz, 3H), 1.39 (d, J=7.1 Hz, 3H), 1.78-1.87 (m, 2H), 1.89-2.03 (m, 2H), 2.25 (td, J=6.8 Hz, 11.6 Hz, 1H), 2.37-2.54 (m, 2H), 2.77 (td, J=5.8 Hz, 17.2 Hz, 1H), 3.41 (dd, J=1.3 Hz, 3.0 Hz, 1H), 3.99 (d, J=3.0 Hz, 1H), 5.00 (sept, J=6.3 Hz, 1H).

$^{13}$C NMR (CDCl$_3$, 100 MHz) δ (major isomer) 21.04, 21.77 (2C), 23.46, 23.73, 25.91, 26.09, 43.39, 49.29, 72.68, 101.48, 134.30, 149.45, 153.51, 156.71, 157.31.

Example P9

Preparation of the Compound of Formula XIIe

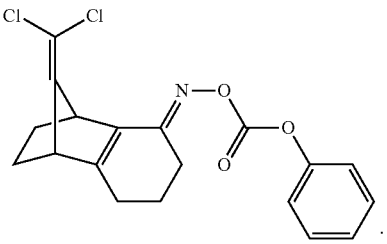

(XIIe)

A mixture of the compound of formula VIII (10.43 g, 0.040 mol) and triethylamine (4.47 g, 0.044 mol) in toluene (50 g) was treated with a solution of phenyl chloroformate (7.10 g, 0.45 mol) in toluene (10 g) at 25° C. within 60 min and stirred at 25° C. for additional 4 h. The reaction mixture was treated with water (30 g). The organic layer was separated and the aqueous layer was re-extracted with toluene (50 g). The combined organic layers were evaporated to dryness. The remaining yellow solid (15.5 g) was dissolved in hot isopropanol (105 g) and slowly cooled down to 5° C. The resulting precipitate was filtered off, washed with cold isopropanol and dried in vacuum. Yield 12.9 g (85%, 99+% purity as determined by quantitative $^1$H NMR and LC analyses).

M. p. 143° C.

$^1$H NMR (CDCl$_3$, 400 MHz) δ (major isomer) 1.27-1.41 (m, 2H), 1.82-1.89 (m, 2H), 1.92-2.04 (m, 2H), 2.28 (td, J=6.8 and 18.4 Hz, 1H), 2.44 (td, J=5.3 and 18.4 Hz, 1H), 2.56 (td, J=7.3 and 17.2 Hz, 1H), 2.84 (td, J=5.8 and 17.1 Hz, 1H), 3.46 (dd, J=1.0 and 3.5 Hz, 1H), 4.02 (d, J=3.0 Hz, 1H), 7.23-7.30 (m, 3H), 7.36-7.45 (m, 2H).

$^{13}$C NMR (CDCl$_3$, 100 MHz) δ (major isomer) 21.04, 23.50, 23.80, 25.90, 26.10, 43.42, 49.36, 101.68, 120.95 (2C), 126.11, 129.52 (2C), 134.05, 149.37, 151.05, 152.24, 157.65, 158.25.

Example P10

Preparation of the Compound of Formula XIIf

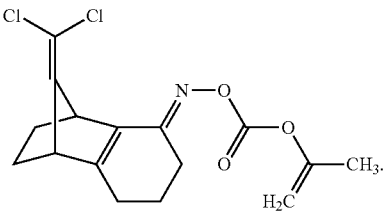

(XIIf)

A mixture of the compound of formula VIII (7.8 g, 0.030 mol) and triethylamine (3.4 g, 0.034 mol) in toluene (50 g) was treated with isopropenyl chloroformate (4.0 g, 0.033 mol) at 25° C. within 60 min and stirred at 25° C. for additional 100 min. The resulting precipitate was filtered off and washed with toluene (2×10 g). The combined washings were evaporated to dryness and the solid was dried in vacuum. Yield 10.3 g (99%, 98+% purity as determined by quantitative $^1$H NMR and LC analyses)

M. p. 155° C. .

¹H NMR (CDCl₃, 400 MHz) δ (major isomer) 1.24-1.38 (m, 2H), 1.78-1.86 (m, 2H), 1.88-2.04 (m, 2H), 2.02 (s, 3H), 2.25 (td, J=6.6 and 18.5 Hz, 1H), 2.35-2.54 (m, 2H), 2.78 (td, J=5.8 and 17.2 Hz, 1H), 3.42 (dd, J=0.8 and 3.3 Hz, 1H), 3.98 (d, J=3.0 Hz, 1H), 4.75 (q, J=0.8 Hz, 1H), 4.87 (q, J=1.5 Hz, 1H).

¹³C NMR (CDCl₃, 100 MHz) δ (major isomer) 19.12, 21.01, 23.46, 23.71, 25.88, 26.08, 43.37, 49.32, 101.58, 102.34, 134.05, 149.37, 151.54, 152.91, 157.40, 157.95.

Example P 11

Preparation of 3-difluoromethyl-1-methyl-1H-pyrazole-4-carboxylic acid (9-dichloromethylene-1,2,3,4-tetrahydro-1,4-methano-naphthalen-5-yl)-amide of formula I

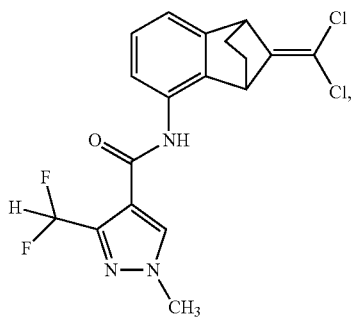
(I)

A mixture of the compound of formula VIII (31.2 g, 0.120 mol) and triethylamine (13.4 g, 0.132 mol) in xylene (mixture of isomers) (120 g) was treated with ethyl chloroformate (15.9 g, 0.147 mol) at 25° C. within 30 min and stirred at 25° C. for additional 30 min. The reaction mixture was treated successively with a solution of the compound of formula IX (24.5 g, 0.126 mol) in xylene (mixture of isomers) (57 g) and with MeSO₃H (1.15 g, 0.012 mol) at 25° C. in single portions. The reaction mixture was heated to 110° C. under a slight vacuum (300-400 mbar) within 75 min and stirred at 110° C. for additional 2 hours, in which ca. 75 g of a distillate were removed from the reaction mixture. The mixture was cooled down to 60-70° C., treated successively with water (13 g) and 30% (w/w) aqueous NaOH solution (22 g) and stirred at 60-70° C. for 30 min. More xylene (mixture of isomers) (40 g) and water (5 g) were added to the mixture at 60-70° C. The organic layer was separated at 75-80° C. and the aqueous layer was re-extracted with xylene (mixture of isomers) (15 g). The combined organic layers were heated to 90° C. at 230 mbar to remove ca. 68 g of a distillate. The mixture was treated with methycyclohexane (57 g) at 85-90° C., inoculated and cooled down to 5° C. within 8 h. The resulting precipitate was filtered off, washed with methycyclohexane and dried in vacuum. Yield 42.2 g (87%, >98% purity as determined by quae ¹H NMR and LC analyses).

¹H NMR (CDCl₃, 400 MHz) δ 1.37 (m, 1H), 1.49 (m, 1H), 2.09 (m, 2H), 3.90 (s, 3H), 3.94 (m, 1H), 4.07 (m, 1H), 6.91 (t, =54.2 Hz, 1H), 7.02 (d, J=7.3 Hz, 1H), 7.16 (t, J=7.8 Hz, 1H), 7.79 (d, J=8.2 Hz, 1H), 8.01 (s, 1H), 8.15 (m, 1H). The compound 3-difluoromethyl-1-methyl-1H-pyrazole-4-carboxylic acid [2-dichloromethylene-1-hydroxy-3-(2-hydroxy-ethyl)-indan-4-yl]-amide was not found in the final product.

What is claimed is:
1. A process for the preparation of the compound of formula I

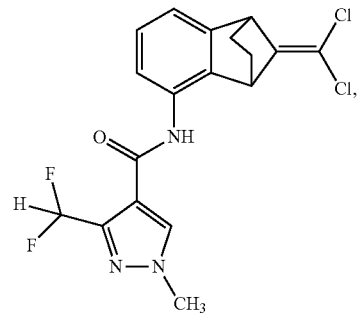
(I)

which process comprises
acylating the oxime oxygen of the compound of formula VIII

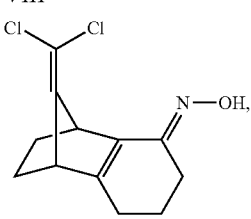
(VIII)

in the presence of a solvent and an acylating agent of formula XI

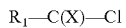
R₁—C(X)—Cl    (XI), wherein X is oxygen or sulfur;
R₁ is chloro if X is oxygen or sulfur; or
R₁ is C₁-C₆alkoxy, CH₃—C(=CH₂)—O—, phenoxy or trichloromethoxy if X is oxygen;
and
a) if R₁ is chloro and the compound of formula XI was added to the compound of formula VIII;
reacting the so obtained product of formula XIIa

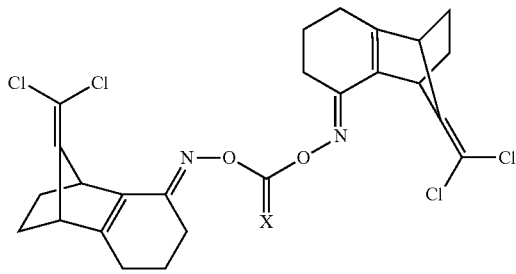
(XIIa)

wherein X is oxygen or sulfur;
with the compound of formula IX

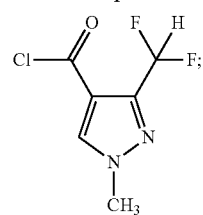
(IX)

or
b) if R₁ is chloro and the compound of formula VIII was added to the compound of formula XI;

or $R_1$ is $C_1$-$C_6$alkoxy, $CH_3$—C(=$CH_2$)—O—, phenoxy or trichloromethoxy if X is oxygen;

reacting the so obtained product of formula XII (XII)

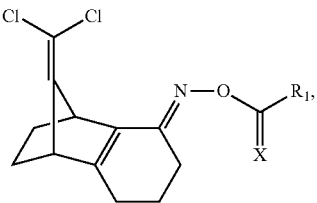

wherein X is oxygen or sulfur;
$R_1$ is chloro if X is oxygen or sulfur; or
$R_1$ is $C_1$-$C_6$alkoxy, $CH_3$—C(=$CH_2$)—O—, phenoxy or trichloromethoxy if X is oxygen;
with the compound of formula IX (IX)

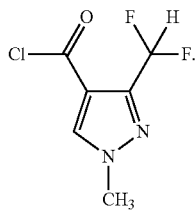

2. A process according to claim 1, wherein the acylating agent is selected from a compound of formula XI, wherein $R_1$ is methoxy, ethoxy, isopropoxy, isopropenyloxy or phenoxy and X is oxygen.

3. A process according to claim 2, wherein the acylating agent is ethyl-chloroformate.

4. A process according to claim 1, wherein the acylated agent is reacted with the compound of formula IX in the presence of an acid.

5. A process according to claim 1, wherein the acylated agent is reacted with the compound of formula IX in the presence of $CH_3SO_3H$.

6. A process according to claim 1, wherein the acylating agent is ethyl-chloroformate and the acylated derivative is reacted with the compound of formula IX in the presence of $CH_3SO_3H$.

7. A compound of formula XII (XII)

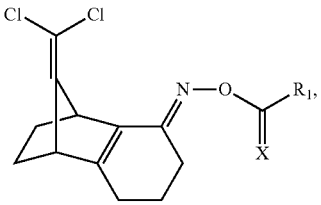

wherein X is oxygen or sulfur;
$R_1$ is chloro if X is oxygen or sulfur; or
$R_1$ is $C_1$-$C_6$alkoxy, $CH_3$—C(=$CH_2$)—O—, phenoxy or trichloromethoxy if X is oxygen.

8. A compound of formula XIIa (XIIa)

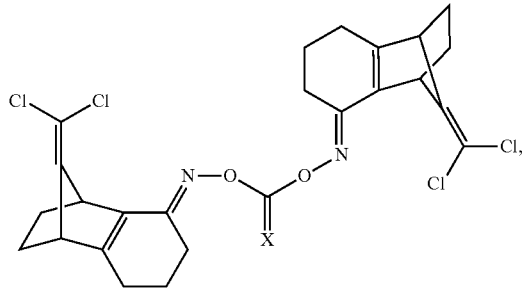

wherein X is oxygen or sulfur.

* * * * *